United States Patent
Pyo et al.

(10) Patent No.: US 7,259,268 B2
(45) Date of Patent: Aug. 21, 2007

(54) METHOD FOR PURIFICATION OF PACLITAXEL FROM PACLITAXEL-CONTAINING MATERIALS

(75) Inventors: Sang-Hyun Pyo, Gongju (KR); Moon-Suk Kim, Busan (KR); Jin-Suk Cho, Daejeon (KR); Bong-Kyu Song, Daejeon (KR); Ho-Joon Choi, Daejeon (KR)

(73) Assignee: Samyang Genex Corporation, Seoul (KR)

( * ) Notice: Subject to any disclaimer, the term of this patent is extended or adjusted under 35 U.S.C. 154(b) by 14 days.

(21) Appl. No.: 11/028,487

(22) Filed: Dec. 30, 2004

(65) Prior Publication Data

US 2005/0154218 A1    Jul. 14, 2005

(30) Foreign Application Priority Data

Dec. 31, 2003  (KR) .................. 10-2003-0101464
Dec. 16, 2004  (KR) .................. 10-2004-0106884

(51) Int. Cl.
C07D 305/00 (2006.01)
C07D 407/00 (2006.01)
C07D 493/00 (2006.01)

(52) U.S. Cl. ...................... 549/510; 549/511
(58) Field of Classification Search ............... 549/510, 549/511
See application file for complete search history.

(56) References Cited

U.S. PATENT DOCUMENTS 5,475,120 A * 12/1995 Rao ............... 549/510
5,900,367 A   5/1999  Hong et al. .......... 435/123
5,969,165 A * 10/1999 Liu ................. 549/510
6,136,989 A * 10/2000 Foo et al. ............ 549/510

FOREIGN PATENT DOCUMENTS

WO    00/40573       7/2000
WO    00/78741 A2   12/2000

OTHER PUBLICATIONS

Zhang, Z., "Separation and Purification of Taxol Using Normal and Reversed Phase Chromatography in Tandem", *Sheng Wu Gong Cheng Xue Bao Chinese Journal of Biotechnology*, vol. 16, No. 1, pp. 69-73 (Jan. 2001) with English-language abstract.
Kim, J., et al. "Development of High Performance Liquid Chromatography for Paclitaxel Purification from Plant Cell Cultures", *Journal of Microbiology and Biotechnology*, vol. 11, No. 2, pp. 204-210 (Apr. 2001).

* cited by examiner

*Primary Examiner*—Thomas McKenzie
*Assistant Examiner*—Niloofar Rahmani
(74) *Attorney, Agent, or Firm*—Ladas & Parry LLP

(57) ABSTRACT

This invention relates to methods for purification of paclitaxel from a paclitaxel-containing material. The method comprises the following steps: (a) extracting a paclitaxel-containing material with an organic solvent to obtain an extract, and concentrating the extract; (b) adding the concentrate with an organic solvent which is not mixed with water to separate an organic solvent phase and then concentrating; (c) subjecting the concentrate to normal phase chromatography to obtain an eluate; (d) dissolving the eluate in an acetone or dichloromethane followed by adding pentane or hexane to form a precipitate; and (e) subjecting the precipitate to high performance liquid chromatography. According to the method of the present invention, paclitaxel of over 99.5% purity can be easily obtained from a *Taxus* genus plant with a high yield.

14 Claims, 2 Drawing Sheets

METHOD FOR PURIFICATION OF PACLITAXEL FROM PACLITAXEL-CONTAINING MATERIALS

CROSS REFERENCE TO RELATED APPLICATION

This application is based on application Nos. 10-2003-0101464 and 10-2004-0106884 filed in the Korean Industrial Property Office on Dec. 31, 2003 and Dec. 16, 2004, the contents of which are incorporated hereinto by reference.

BACKGROUND OF THE INVENTION (a) Field of the Invention

This invention relates to methods for purification of paclitaxel from paclitaxel-containing material.

(b) Description of the Related Art

Paclitaxel is the most important antineoplastic agent for ovarian cancer, breast cancer, etc. discovered in the United States in the 1960's when the National Cancer Institute began a large-scale screening program for selecting material having anti-cancer activity. Paclitaxel has been widely used as an antineoplastic agent since approval by the FDA (Federal Drug & Food Agency) in 1992.

Because paclitaxel is isolated and purified from the bark of Yew trees in which paclitaxel is present in a very low amount (about 0.02%), a high cost in purification of paclitaxel has been demanded, and destruction of nature and ecosystems has been provoked. To overcome the above problems, a method for semi-synthesis of paclitaxel using precursors obtained from the needles of Yew trees and a method for large scale production using a Yew tree-cell culturing method have been developed. The prior arts relating to methods of purification of paclitaxel are as follows.

The procedure of WO 00/40573 of Foo et al. provides a method for preparing a high purity paclitaxel from a paclitaxel-containing material, the method comprising: obtaining a low purity extract by a liquid/liquid extracting procedure; purifying the extract through a silica column; conducting precipitation of the extract with an acetone/aqueous solvent; and repeating the silica column and crystallization steps. However, this procedure needs performing of chromatography three times and of crystallizing two times to acquire high purity paclitaxel. In addition, a precipitation method using an acetone/aqueous solvent should be undertaken in this procedure, and productivity of Paclitaxel is 49–73%, which is very low.

The procedure of WO 00/078741 of Bui-khac et al. provides a method for the extraction and purification of paclitaxel that includes the steps of: a) extracting a raw material comprising paclitaxel with an organic solvent from the natural source of taxanes; b) treating the raw material with a base or acid to obtain a biomass by precipitation; c) percolorizing the biomass by removing resin and natural pigment contained therein; and d) chromatographically purifying at least once and crystallizing at least once by adding acetone and hexane. However, it is known that paclitaxel is decomposed to 10-deacetylpaclitaxel and baccatin III in an acidic or base condition. Therefore, this method has difficulty in purifying paclitaxel with a high yield, and needs much time because of complicated procedures.

The procedure of U.S. Pat. No. 5,900,367 of Hong et al. provides a method for mass production of paclitaxel. The steps include: a) synthetic absorbent treatment of a crude extract, prepared by a method of organic solvent extraction, to remove a tar component; b) addition of hexane to the filtrate to precipitate crude taxol; c) fractional precipitation of the crude taxol in a mixture of alcohol and water, and drying the precipitate to obtain taxol powder; and d) high performance liquid chromatography of the taxol powder. This method has an advantage in isolation and purification of high purity with a small quantity of solvent by using only three extracting and purifying solvents: dichloromethane, methanol, and hexane. However, there is a need for re-fractional precipitation of the filtrate recovered from precipitation solution to enhance purity and fractional precipitation yield.

SUMMARY OF THE INVENTION

It is an object of the present invention to provide a method for effective extraction and purification of paclitaxel from a paclitaxel-containing material.

It is another object of the present invention to provide a simple and easy method for isolating paclitaxel with high purity.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, wherein.

DETAILED DESCRIPTION OF THE PREFERRED EMBODIMENTS

Figure 1:
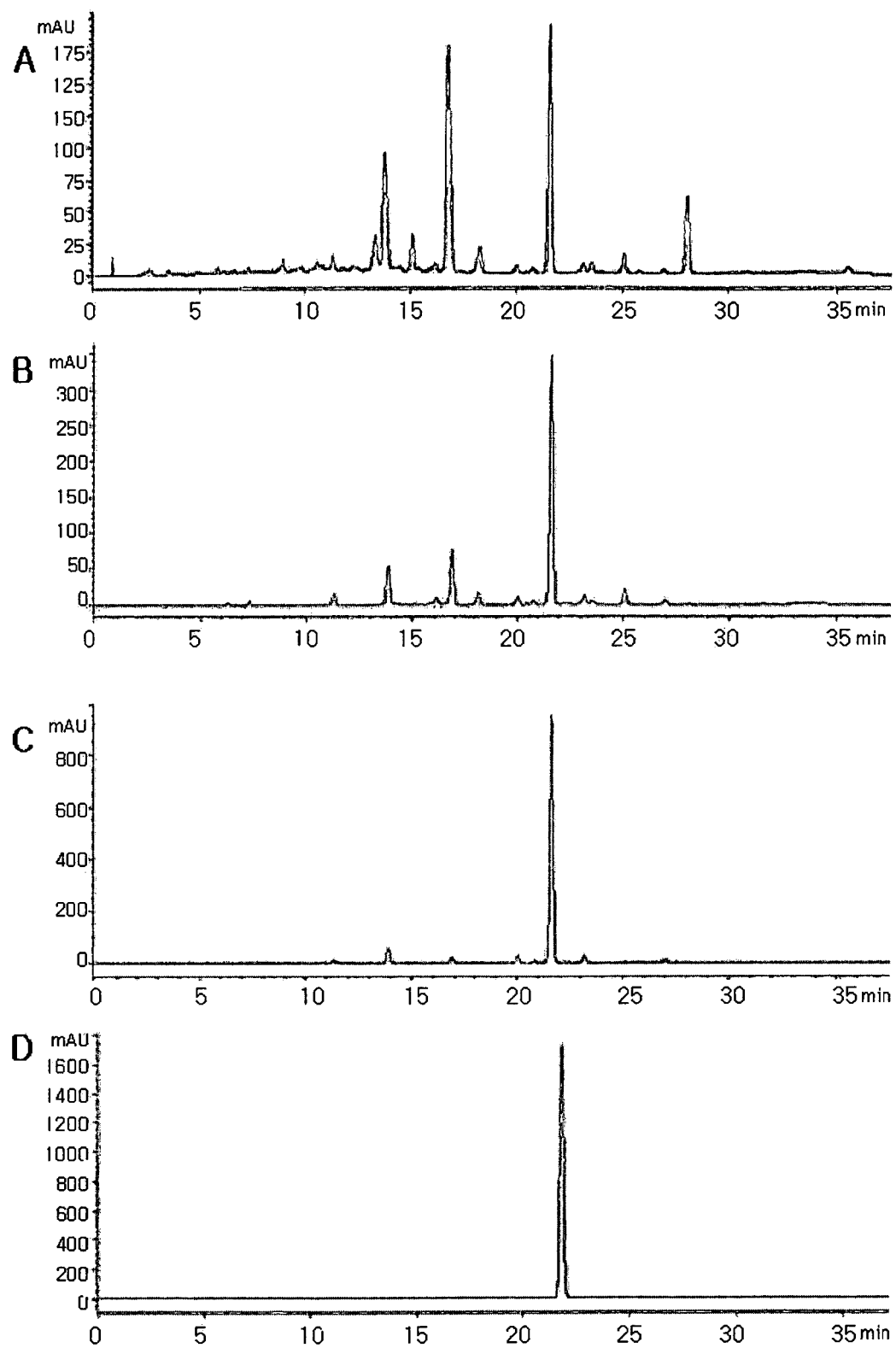
FIG. 1 is a HPLC chart showing a purity and yield of paclitaxel according to each step of the purification procedure.

In the following detailed description, only selected embodiments of the invention have been shown and described, simply by way of illustration of the best mode contemplated by the inventors of carrying out the invention. As will be realized, the invention may be modified in various respects, all without departing from the invention. Accordingly, the drawings and description are to be regarded as illustrative in nature, and not restrictive.

The present invention relates to a method for purifying paclitaxel from paclitaxel-containing material.

Paclitaxel-containing material suitable for the present invention includes plants belonging to *Taxus* genus, or cell cultures thereof, including tissue, cells, or cell-culture solution including a medium. The plants include, but are not limited to, *Taxus brevifolia, Taxus canadensis, Taxus cuspidate, Taxus baccata, Taxus globosa, Taxus floridana, Taxus wallichiana, Taxus media, Taxus chinensis*, and the like.

The method for purifying paclitaxel of the present invention includes: (a) extracting a paclitaxel-containing material with an organic solvent to obtain an extract, and concentrating the extract; (b) adding an organic solvent to the concentrate to separate an organic solvent phase, and then concentrating the separated organic solvent phase; (c) conducting the concentrate to normal phase chromatography to separate an eluate; (d) dissolving the eluate in acetone or dichloromethane, followed by adding a pentane or hexane to form a precipitate; and (e) subjecting the precipitate to high performance liquid chromatography.

Another method for purifying paclitaxel of the present invention includes: (a) extracting a paclitaxel-containing material with an organic solvent to obtain an extract, and concentrating the extract; (b) adding an organic solvent to the concentrate to separate an organic solvent phase, and then concentrating the separated organic solvent phase; (c) conducting the concentrate to normal phase chromatography to separate an eluate; (d') dissolving the eluate in methanol, followed by adding water to form a precipitate; and (e) subjecting the precipitate of the step (d') to high performance liquid chromatography.

In the above (a) step, the organic solvent can be selected at least one, but is not limited thereto, from the group consisting of methanol, ethanol, propanol, and dichloromethane. The preferred exemplary solvent is methanol. The solvent may be added in an amount of about 20~200% (v/w), preferably 40~140% (v/w), to the paclitaxel-containing material, followed by being agitated for about 30 minutes at room temperature and purified at least twice to extract paclitaxel and taxane derivatives. The extracts may be concentrated by a vacuum concentrator or the like.

In the above (b) step, an organic solvent is added in an amount of about 10~50% (v/v), preferably 20~30% (v/v), to the extract or the extract concentrate of the (a) step, followed by agitation to isolate an organic solvent phase. The step for isolating an organic solvent phase may be repeated at least twice and the isolated organic solvent phase is vacuum concentrated and dried. The organic solvent of the (b) step that is used is not mixed with water. For example, the organic solvent in the (b) step may be a non-polar organic solvent and may include: an alkylhalide, such as dichloromethane, carbon tetrachloride, chloroform, 1,2-dichloroethane, and the like; an ether such as di-ethyl ether, methyl-t-butyl ether, di-iso-propyl ether, and the like; alcohols of $C_4$–$C_6$, such as n-butanol, n-pentanol, and the like; ethyl acetate; or a methyl ethyl ketone, and the like. A part of the polar substance is removed through the step (b).

In the above (c) step, the dried extract of the (b) step is dissolved in organic solvent to subject it to normal phase column chromatography. A column packing material that may be used in the present invention is a generally used silica gel, for example, a silica gel 40 (63~200 µm), a silica gel 60 (63~200 µm), or a silica gel 60F254 (200~500 µm). An organic solvent suspending the dried extract may be at least one selected from the group consisting of dichloromethane, methanol, benzene, acetone, hexane, and ethyl acetate. In normal phase column chromatography, fractions can be obtained through an isocratic elution or a step-gradient elution. In the isocratic elution, the elution solvent in which methanol and dichloromethane are mixed at a volume ratio of 0.5~10:99.5~90 can be used. In the gradient elution, the equilibrium solvent in which dichloromethane or methanol and dichloromethane are mixed at a volume ratio of 0.1~5:99.9~95 can be used, and an eluting solvent in which 0.5~100% (v/v) of methanol and the rest of dichloromethane are mixed can be used.

The 'isocratic elution' is a method using a solvent without changing concentration of the solvent, and the 'gradient elution' means an eluting method changing a concentration of a solvent gradationally.

In the above (c) step, a procedure of vacuum concentrating and drying of an eluate, a result of normal phase chromatography, can be further conducted. The above normal phase chromatography, as a procedure taking the place of the synthetic adsorbent treating procedure and the precipitation procedure with a hexane, can simplify a purification procedure and notably enhance yield of paclitaxel. In addition, a precipitate can be obtained with easy and high yield through the precipitation procedure from the fraction yielded with normal phase chromatography.

In the above (d) step, the dried eluate of the (c) step is dissolved in acetone or dichloromethane and then added to a pentane or a hexane to form a precipitate. Acetone or dichloromethane can dissolve about 5~100 mg of dried eluate per 1 ml. The blending ratio of a pentane or a hexane to acetone or dichloromethane may include a volume ratio of 1:1~20, preferably 1:5~10. A time for the precipitation process after adding the pentane or hexane may be, but is not limited to, about 1~5 days, preferably about 1~2 days; and the temperature is lower than 35° C., preferably about 0~15° C. A precipitate is obtained following a common filtration method.

In the above (d') step, the dried eluate of the (c) step is dissolved in methanol and then added to water to form a precipitate. The methanol can dissolve about 5~100 mg of dried eluate per 1 ml. Water and methanol can be mixed at a volume ratio of about 1:1~20, preferably about 1:5~10. A time and temperature after adding the pentane or hexane may be, but is not limited to, about 1~5 days, preferably abut 2~3 days, and lower than 35° C., preferably about 0~15° C. A precipitate is obtained following a common filtration method.

In the above (e) step, the precipitate of the step (d) or (d') is purified with high performance liquid chromatography. A column packing material that may be used in the present invention is a hydrophobic resin, for example, a non-polar impurity removing ODS (Octadecylsilylated $C_{18}$), $C_8$, or $C_4$, and high performance liquid chromatography can be subjected by reverse phase. The elution solvent for chromatography includes 55~75% (v/v) of methanol and the rest of water. The eluted fraction through the reverse phase chromatography is further purified with the second normal phase chromatography packing silica for removing polar impurities. The solvent for the second chromatography includes 95~99% (v/v) of dichloromethane and the rest of methanol, and high purity paclitaxel with about 99.5% purity can be obtained.

According to the method of the present invention, it is possible to obtain paclitaxel of over 99.5% purity with a yield of at least 65.4%, preferably 80.7%.

The range of purity and yield of paclitaxel in the sample to be obtained per step according to the present invention are indicated in Table 1.

TABLE 1

| Steps | Purity (%) | Yield (%) |
|---|---|---|
| Starting Paclitaxel-containing material | 0.01–0.05 | 100 |
| (a) step: methanol extraction | 0.1–0.5 | 93–97 |
| (b) step: liquid—liquid extraction | 3.0–9.0 | 95–96 |
| (c) step: normal phase column chromatography | 20–35 | 95–97 |
| (d) step: acetone/pentane precipitation | 65–85 | 92–97 |
| (d') step: methanol/water precipitation | 52–82 | 89–92 |
| (e) step: reverse phase high performance liquid chromatography | 90–98 | 93–96 |
| (e) step: normal phase high performance liquid chromatography | 99.5–99.9 | 92–96 |
| Final | 99.5–99.9 | 65.4–80.7 |

The above purity and yield of paclitaxel is quantitatively analyzed in the conditions in the following Table 2.

TABLE 2

| | |
|---|---|
| Instrument | Hewlett Packard 1090 HPLC |
| Column | Curosil PFP 4.6–250 |
| Temperature of column | 35° C. |
| Mobile phase | Acetonitrile: water (35–65% concentrate gradient) |
| Flow velocity | 1 ml/min |
| Amount of injection | 10 μl |
| Detector | UV(227 nm) |

FIG. 1 is an HPLC chart showing purity and yield of paclitaxel. (A) is an HPLC chart for the product after extracting an organic solvent of the (b) step, (B) is an HPLC chart for the product after normal phase chromatography of the (c) step, (C) is an HPLC chart for the product after precipitating acetone/pentane of the (d) step, and (D) is an HPLC chart for the product after high performance liquid chromatography of the (e) step.

Figure 2A:
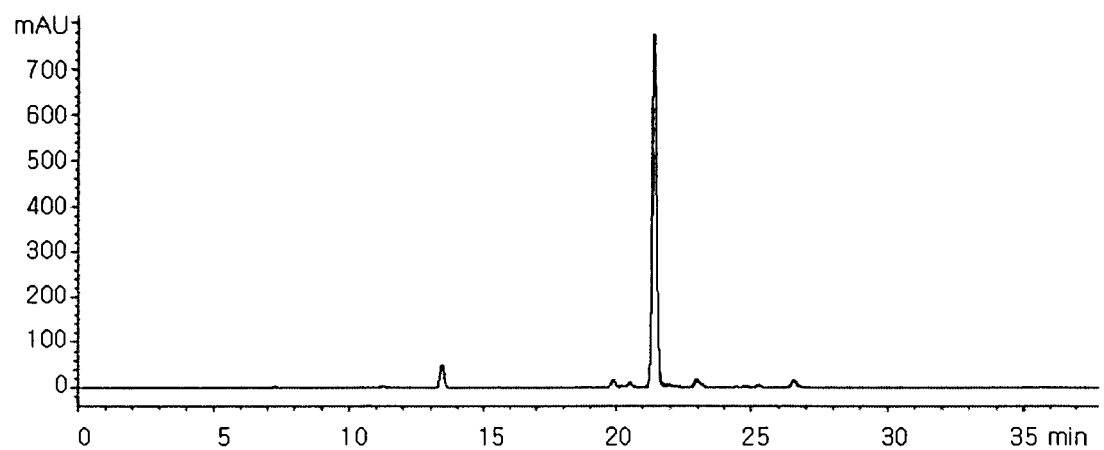
FIG. 2a is a HPLC chart of a sample after the step (d') of methanol/water precipitation.
Figure 2B:
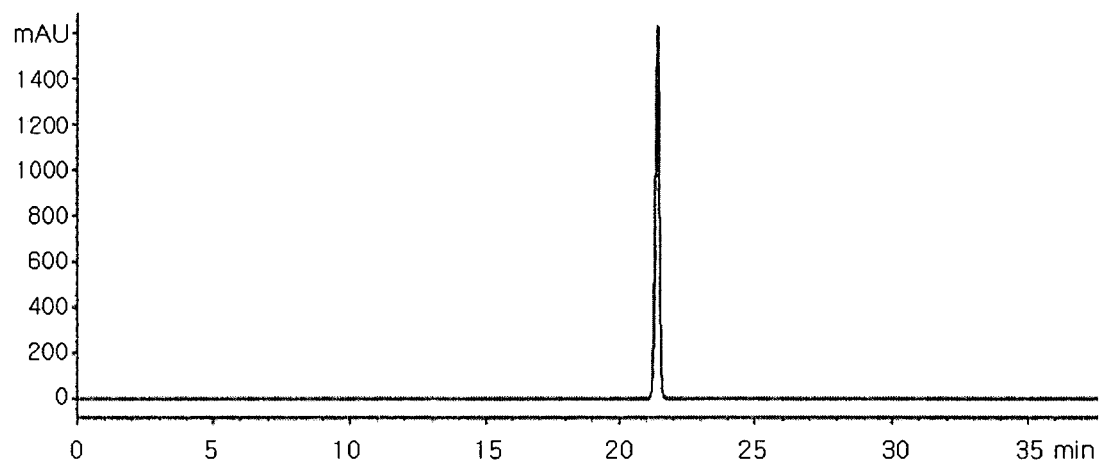
FIG. 2b is a HPLC chart showing a purity and yield of paclitaxel after the step (e).

FIGS. 2a and 2b show the results of HPLC confirmable purity and yield of paclitaxel after the steps (d') and (e).

The following examples are provided to further illustrate the present invention and are not intended to limit the invention beyond the limitations set forth in the appended claims.

EXAMPLE 1

Organic Solvent Extraction and Liquid-Liquid Extraction of Plant Cell Cultures

110 L of methanol was added to 100 kg of plant cells obtained by culturing SYG-1 (KCTC-0232BP) originated from *Taxus chinensis*, and then stirred for about 30 minutes at room temperature followed by filtration. Methanol extracts were obtained after repeating the above extracting procedure 4 times, and the extracts were vacuum concentrated to obtain about 20 L of concentrate. 5400 ml of dichloromethane was added to the concentrate followed by agitation, and then a dichloromethane phase was separated. The separated dichloromethane phase was vacuum concentrated and dried to give 737 g of dried extract of 6.9% purity.

EXAMPLE 2

Normal Phase Chromatography (Isocratic Elution)

15 g of the dried extract of EXAMPLE 1 dissolved in 200 ml of dichloromethane was injected into a 19 mm (diameter)×900 mm (length) stainless steel column packed with silica gel 60N (Timely Co., Japan), and eluted with a mixture of methanol and dichloromethane of 1%:99%(v/v), 1.5%:98.5%(v/v), and 2%:98%(v/v), respectively. The eluates were fractionized. Table 3 shows purity and yield of paclitaxel in the elution fraction.

TABLE 3

| No. experiment | % (v/v) methanol/dichloromethane | Purity (%) | Yield (%) |
|---|---|---|---|
| A | 1.0/99.0 | 32.6 | 84.0 |
| B | 1.5/98.5 | 31.8 | 90.5 |
| C | 2.0/98.0 | 30.7 | 97.5 |

EXAMPLE 3

Normal Column Chromatography (Gradient Elution)

15 g of the dried extract of EXAMPLE 1 dissolved in 200 ml of dichloromethane was loaded into a 19 mm (diameter)×900 mm (length) stainless steel column packed with silica gel 60N (Timely Co., Japan), equilibrated with dichloromethane, a mixture of methanol and dichloromethane of 0.5:99.5% (v/v), and a mixture of methanol and dichloromethane of 1:99% (v/v) respectively, and eluted with a mixture of methanol and dichloromethane of 2:98% (v/v). An elution fraction was recovered and the purity and yield of paclitaxel in the recovered elution fraction is shown in Table 4.

TABLE 4

| No. experiment | solvent, methanol:dichloromethane | Purity (%) | Yield (%) |
|---|---|---|---|
| D | 0:100 | 22.7 | 96.9 |
| E | 0.5/99.5 | 24.2 | 96.5 |
| F | 1.0/99.0 | 25.5 | 97.3 |

EXAMPLE 4

Normal Column Chromatography (Gradient Elution)

The steps of EXAMPLE 3 were carried out on a large scale.

510 g of the dried extract of EXAMPLE 1 dissolved in 5600 ml of dichloromethane applied into a 100 mm (diameter)×900 mm (length) stainless steel column packed with a silica gel 60N (Shiseido Co., Japan), equilibrated with a mixture of methanol and dichloromethane of 1:99% (v/v) and eluted with a mixture of methanol and dichloromethane of 2:98% (v/v). The fraction was vacuum concentrated to obtain 99.9 g of dried concentrate, and the purity and yield of paclitaxel purified with the above procedure was 32.2% and 97.0% respectively.

EXAMPLE 5

Acetone/Pentane Precipitation 2 ml of acetone was added to 40 mg of the dried concentrate of EXAMPLE 4, and then 6, 8, 10, 12, 14, 16, and 18 ml of pentane was added respectively and left for 48 hours at 4° C. A precipitate was then recovered, and the purity and yield of paclitaxel in the precipitate is shown in Table 5.

TABLE 5

| | Starting material | | | | precipitate | |
|---|---|---|---|---|---|---|
| No. of experiment | Purity (%) | Weight (mg) | Acetone, ml | Pentane, ml | Purity (%) | Yield (%) |
| G | 32.2 | 40 | 2 | 6 | 85.1 | 82.2 |
| H | 32.2 | 40 | 2 | 8 | 81.4 | 83.9 |
| I | 32.2 | 40 | 2 | 10 | 79.8 | 95.4 |
| J | 32.2 | 40 | 2 | 12 | 77.4 | 96.5 |
| K | 32.2 | 40 | 2 | 14 | 77.1 | 96.6 |
| L | 32.2 | 40 | 2 | 16 | 76.5 | 97.6 |
| M | 32.2 | 40 | 2 | 18 | 70.4 | 97.6 |

EXAMPLE 6

Acetone/Pentane Precipitation

Precipitation was carried out in accordance with EXAMPLE 5 under the conditions described in Table 6. The result of precipitation is shown in Table 6.

TABLE 6

| No. of experiment | Starting material | | | | precipitate | |
|---|---|---|---|---|---|---|
| | Purity (%) | Weight (mg) | Acetone, ml | Pentane, ml | Purity (%) | Yield (%) |
| N | 32.2 | 10 | 2 | 12 | 74.7 | 83.7 |
| O | 32.2 | 20 | 2 | 12 | 79.5 | 93.4 |
| P | 32.2 | 40 | 2 | 12 | 77.4 | 96.5 |
| Q | 32.2 | 80 | 2 | 12 | 54.5 | 98.9 |

EXAMPLE 7

Acetone/Pentane Precipitation

The dried concentrate of the fraction having variable purity recovered from normal phase chromatography was precipitated in accordance with EXAMPLE 5, under the conditions described in Table 7. The result of precipitation is shown in Table 7.

TABLE 7

| No. of experiment | Starting material | | | | precipitate | |
|---|---|---|---|---|---|---|
| | Purity (%) | Weight (mg) | Acetone, ml | Pentane, ml | Purity (%) | Yield (%) |
| R | 10.2 | 40 | 2 | 12 | 24.4 | 85.4 |
| S | 15.4 | 40 | 2 | 12 | 50.2 | 90.3 |
| T | 21.7 | 40 | 2 | 12 | 62.4 | 96.5 |
| U | 30.1 | 40 | 2 | 12 | 74.2 | 98.8 |
| V | 50.2 | 40 | 2 | 12 | 73.8 | 98.5 |

EXAMPLE 8

Acetone/Hexane Precipitation

The dried concentrate of the fraction having different purity recovered from normal phase chromatography was precipitated in accordance with EXAMPLE 5 except for using hexane instead of pentane, especially under the conditions described in Table 8. The result of precipitation is shown in Table 8.

TABLE 8

| No. of experiment | Starting material | | | | precipitate | |
|---|---|---|---|---|---|---|
| | Purity (%) | Weight (mg) | Acetone, ml | Hexane, ml | Purity (%) | Yield (%) |
| W | 30.0 | 20 | 2 | 12 | 72.1 | 95.4 |
| X | 45.8 | 20 | 2 | 12 | 75.4 | 96.2 |

EXAMPLE 9

Dichloromethane/Hexane Precipitation

The dried concentrate of the fraction having different purity recovered from normal phase chromatography was precipitated in accordance with EXAMPLE 5 except for using dichloromethane instead of acetone and hexane instead of pentane, especially under the conditions described in Table 9. The result of precipitation is showed in Table 9.

TABLE 9

| No. of experiment | Starting material | | Dichloromethane, ml | Hexane, ml | precipitate | |
|---|---|---|---|---|---|---|
| | Purity (%) | Weight (mg) | | | Purity (%) | Yield (%) |
| Y | 30.0 | 20 | 2 | 20 | 52.7 | 93.4 |
| Z | 48.3 | 20 | 2 | 20 | 72.4 | 91.6 |

EXAMPLE 10

Methanol/Water Precipitation

The dried concentrate of the fraction having different purity recovered from normal phase chromatography was dissolved in methanol under the conditions described in Table 10 and left for 3 days at 4° C. after adding purified water thereto. The precipitate was filtered and the weight and purity of paclitaxel in the precipitate was evaluated. The result of precipitation is shown in Table 10.

TABLE 10

| No. of experiment | Starting material | | Methanol, ml | Water, ml | precipitate | |
|---|---|---|---|---|---|---|
| | Purity (%) | Weight (mg) | | | Purity (%) | Yield (%) |
| 1 | 32.2 | 1.0 | 100 | 250 | 52.2 | 90.5 |
| 2 | 34.4 | 0.2 | 7 | 4.7 | 70.7 | 89.8 |
| 3 | 49.1 | 0.2 | 10 | 6.7 | 81.1 | 91.9 |

EXAMPLE 11

High Performance Liquid Chromatography

The dried extract of experiment NO. J in EXAMPLE 5 dissolved in 70% methanol was injected into ODS($C_{18}$) of reverse phase high performance liquid chromatography and eluted with a mixture of methanol and purified water of 65%:35% (v/v). The purity and yield of paclitaxel in the fraction were 95% and 95%, respectively.

The fraction was injected into a high performance liquid chromatograph packed with silica and eluted with a mixture of dichloromethane and methanol of 98%:2% (v/v) to obtain an eluate. The purity and yield of paclitaxel in the eluate were 99.5% and 95%, respectively.

In addition, the precipitate of experiment No. 1 in EXAMPLE 10 was purified in accordance with the same procedure as above, and the purity and yield of paclitaxel in the fraction were 99.5% and 94%. respectively.

Therefore, the method of the present invention can be of use in production of paclitaxel by virtue of easy isolation of paclitaxel with a high purity as well as a high yield.

What is claimed is:

1. A method of purifying paclitaxel, consisting essentially of:
   (a) extracting a plant belonging to a *Taxus* genus, a cell, or a cell culture thereof, with an organic solvent to obtain an extract, and concentrating the extract;
   (b) adding an organic solvent which is not mixed with water to the concentrate to separate an organic solvent phase and then concentrating;
   (c) subjecting the concentrate to normal phase chromatography to obtain an eluate;
   (d) dissolving the eluate in an acetone or dichloromethane followed by adding pentane or hexane to form a precipitate, wherein about 5 to 100 mg of the eluate is dissolved in 1 ml of acetone or dichloromethane, and pentane or hexane is added in an amount such that the precipitate upon subjecting to high performance liquid chromatography yields paclitaxel of at least 99.5% purity;
   (e) subjecting the precipitate to high performance liquid chromatography; and
   (f) recovering paclitaxel of at least said purity, wherein the volume ratio of acetone or dichloromethane to pentane or hexane is in a range of 1:3 to 1:20.

2. The method of claim 1, wherein the organic solvent of the step (a) is at least one selected from the group consisting of methanol, ethanol, propanol, and dichloromethane.

3. The method of claim 1, wherein the organic solvent of the step (b) is selected from the group consisting of an alkylhalide, ether, alcohols of $C_4$–$C_6$, ethyl acetate, and methyl ethyl ketone.

4. The method of claim 3, wherein the organic solvent of the step (b) is selected from the group consisting of dichloromethane, carbon tetrachloride, chloroform, 1,2-dichloroethane, di-ethyl ether, methyl-t-butyl ether, di-iso-propyl ether, n-butanol, and n-pentanol.

5. The method of claim 1, wherein the concentrate of the step (c) is dissolved in at least one solvent selected from the group consisting of dichloromethane, methanol, benzene, acetone, hexane, and ethyl acetate.

6. The method of claim 1, wherein the elution of the step (c) is subjected with a mixture of methanol and dichloromethane of 0.5~10%:99.5~90% (v/v).

7. The method of claim 1, wherein equilibrium solvent of the step (c) comprises 0.1~5% (v/v) of methanol and 99.9~95% (v/v) of dichloromethane, and the elution solvent comprises 0.5~100% (v/v) of methanol and the rest of dichloromethane.

8. A method of purifying paclitaxel, consisting essentially of the steps of:
   (a) extracting a plant belonging to a *Taxus* genus, a cell, or a cell culture thereof, with an organic solvent to obtain an extract, and concentrating the extract;
   (b) adding an organic solvent which is not mixed with water to the concentrate to separate an organic solvent phase and then concentrating;
   (c) subjecting the concentrate to normal phase chromatography to obtain an eluate;
   (d) dissolving the eluate in methanol followed by adding water to form a precipitate, wherein about 5 to 100 mg of the eluate is dissolved in 1 ml of methanol, and water is added in an amount such that the precipitate upon subjecting to high performance liquid chromatography yields paclitaxel of at least 99.5% purity;
   (e) subjecting the precipitate to high performance liquid chromatography; and
   (f) recovering paclitaxel of at least said purity, wherein the volume ratio of methanol to water is in a range of 1:3 to 1:20.

9. The method of claim 8, wherein the organic solvent of the step (a) is at least one selected from the group consisting of methanol, ethanol, propanol, and dichloromethane.

10. The method of claim 8, wherein the organic solvent of the step (b) is selected from the group consisting of an alkylhalide, ether, alcohols of $C_4$–$C_6$, ethyl acetate, and methyl ethyl ketone.

11. The method of claim 10, wherein the organic solvent of the step (b) is selected from the group consisting of dichloromethane, carbon tetrachloride, chloroform, 1,2-dichloroethane, di-ethyl ether, methyl-t-butyl ether, di-iso-propyl ether, n-butanol, and n-pentanol.

12. The method of claim 8, wherein the concentrate of the step (c) is dissolved in at least one solvent selected from the group consisting of dichloromethane, methanol, benzene, acetone, hexane, and ethyl acetate.

13. The method of claim 8, wherein the elution of the step (c) is subjected with a mixture of methanol and dichloromethane of 0.5~10%:99.5~90% (v/v).

14. The method of claim 8, wherein equilibrium solvent of the step (c) comprises 0.1~5% (v/v) of methanol and 99.9~95% (v/v) of dichloromethane, and the elution solvent comprises 0.5~100% (v/v) of methanol and the rest of dichloromethane.

* * * * *